US007014768B2

(12) United States Patent
Li et al.

(10) Patent No.: US 7,014,768 B2
(45) Date of Patent: Mar. 21, 2006

(54) PROCESS FOR REMOVAL AND RECOVERY OF NUTRIENTS FROM DIGESTED MANURE OR OTHER ORGANIC WASTES

(75) Inventors: Xiaomei Li, Edmonton (CA); Le Zeng, Vegreville (CA); Earl August Jenson, Vegreville (CA)

(73) Assignee: Alberta Research Council Inc., Edmonton (CA)

(*) Notice: Subject to any disclaimer, the term of this patent is extended or adjusted under 35 U.S.C. 154(b) by 0 days.

(21) Appl. No.: 10/760,725

(22) Filed: Jan. 20, 2004

(65) Prior Publication Data

US 2004/0164021 A1    Aug. 26, 2004

(30) Foreign Application Priority Data

Jan. 20, 2003  (CA) .................................. 2416690

(51) Int. Cl.
   C02F 3/28      (2006.01)
   C05F 3/00      (2006.01)
(52) U.S. Cl. .................. 210/603; 210/631; 210/903; 210/906; 71/10; 71/21
(58) Field of Classification Search ............. 210/603, 210/612, 613, 631, 903, 906; 71/10, 21; 423/157.5, 220
   See application file for complete search history.

(56) References Cited

U.S. PATENT DOCUMENTS

| 1,999,973 | A | * | 4/1935 | Genter ..................... 210/609 |
| 3,296,122 | A | * | 1/1967 | Karassik et al. ............ 210/603 |
| 3,440,166 | A | * | 4/1969 | Davis et al. ................ 210/603 |
| 3,824,185 | A | * | 7/1974 | Caldwell et al. ........... 210/603 |
| 4,076,515 | A | * | 2/1978 | Rickard ...................... 71/10 |
| 4,204,842 | A | * | 5/1980 | Morel et al. ............... 48/197 A |
| 4,366,059 | A | | 12/1982 | Witt et al. ................. 210/615 |
| 4,415,453 | A | | 11/1983 | Witt et al. ................. 210/615 |
| 4,750,454 | A | | 6/1988 | Santina et al. ............... 123/3 |
| 4,765,900 | A | | 8/1988 | Schwoyer et al. .......... 210/603 |
| 5,360,546 | A | | 11/1994 | Tomita et al. ............. 210/603 |
| 5,378,322 | A | | 1/1995 | Hornsey ..................... 162/158 |
| 5,635,394 | A | | 6/1997 | Horn ......................... 435/266 |
| 5,725,770 | A | | 3/1998 | Henry ........................ 210/603 |
| 5,851,398 | A | | 12/1998 | Adey ......................... 210/602 |
| 5,869,323 | A | | 2/1999 | Horn ......................... 435/266 |

(Continued)

FOREIGN PATENT DOCUMENTS

CA      2248588      9/1997

(Continued)

Primary Examiner—Fred G. Prince
(74) Attorney, Agent, or Firm—Bennett Jones LLP

(57) ABSTRACT

A process for removal and recovery of nutrients and recycling of water from digested manure or other organic wastes. A first step involves separating waste from an anaerobic digester into digested liquids, digested solids, and biogas. A second step involves precipitating solids from the digested liquids. A third step involves stripping ammonia from the digested liquids. A fourth step involves injecting an exhaust stream of carbon dioxide drawn from the co-generator into the digested liquids to reduce the pH and raise the temperature of the digested liquid. A fifth step involves recycling the digested liquids back to the anaerobic digester for use in diluting in coming solid wastes. A sixth step involves passing the excess ammonia stripped from the digested liquid through the digested solids to recover nitrogen through aborption with the resultant digested solids being usable as a biofertilizer with a high nitrogen content. A seventh step involves capturing the biogas for use in a co-generation system.

5 Claims, 2 Drawing Sheets

U.S. PATENT DOCUMENTS

| | | | |
|---|---|---|---|
| 5,993,503 A | 11/1999 | Kruidhof | 72/21 |
| 6,221,254 B1 | 4/2001 | Dickerson et al. | 210/705 |
| 6,299,774 B1 * | 10/2001 | Ainsworth et al. | 210/603 |
| 6,342,378 B1 | 1/2002 | Zhang et al. | 435/168 |
| 6,355,456 B1 | 3/2002 | Hallberg et al. | 435/161 |
| 6,368,849 B1 | 4/2002 | Norddahl | 435/262 |
| 6,409,788 B1 | 6/2002 | Sower | 71/11 |
| 6,464,875 B1 | 10/2002 | Woodruff | 210/603 |
| 6,497,741 B1 | 12/2002 | Sower | 71/11 |
| 6,508,078 B1 | 1/2003 | Sower | 62/532 |
| 2003/0038079 A1 * | 2/2003 | Miller, III | 210/603 |

FOREIGN PATENT DOCUMENTS

| | | |
|---|---|---|
| CA | 2259673 | 7/2000 |
| JP | 10235317 | 9/1998 |
| JP | 2000015229 | 1/2000 |
| WO | 99/42423 | 8/1999 |
| WO | 00/53542 | 9/2000 |
| WO | 02/15945 A1 | 2/2002 |

* cited by examiner

PROCESS FOR REMOVAL AND RECOVERY OF NUTRIENTS FROM DIGESTED MANURE OR OTHER ORGANIC WASTES

FIELD OF THE INVENTION

The present invention relates to a process for removal and recovery of nutrients from digested manure or other organic wastes.

BACKGROUND OF THE INVENTION

Anaerobic digestion of manure and other organic wastes inherently produce by-products which have a negative environmental impact. These by-products are bulky and contain imbalanced nutrients for plant growth.

SUMMARY OF THE INVENTION

What is required is an integrated process for removal and recovery of nutrients from digested manure or other organic wastes that will reduce, if not eliminate, such negative environmental impact.

According to the present invention there is provided a process for removal and recovery of nutrients from digested manure or other organic wastes. A first step involves separating waste from an anaerobic digester into digested liquids, digested solids, and biogas. A second step involves precipitating solids from the digested liquids. A third step involves stripping ammonia from the digested liquids. A fourth step involves injecting a stream of carbon dioxide into the digested liquids to reduce the pH and raise the temperature of the digested liquid. A fifth step involves recycling the digested liquids back to the anaerobic digester for use in diluting in coming solid wastes. A sixth step involves passing the excess ammonia stripped from the digested liquid through the digested solids to recover nitrogen through aborption with the resultant digested solids being usable as a biofertilizer with a high nitrogen content. A seventh step involves capturing the biogas for use in power generation.

It is preferred that the source of carbon dioxide is an exhaust stream of a co-generation system which is fuelled by the captured biogas.

BRIEF DESCRIPTION OF THE DRAWINGS

These and other features of the invention will become more apparent from the following description in which reference is made to the appended drawings, the drawings are for the purpose of illustration only and are not intended to in any way limit the scope of the invention to the particular embodiment or embodiments shown, wherein.

DETAILED DESCRIPTION OF THE PREFERRED EMBODIMENT

Figure 1:
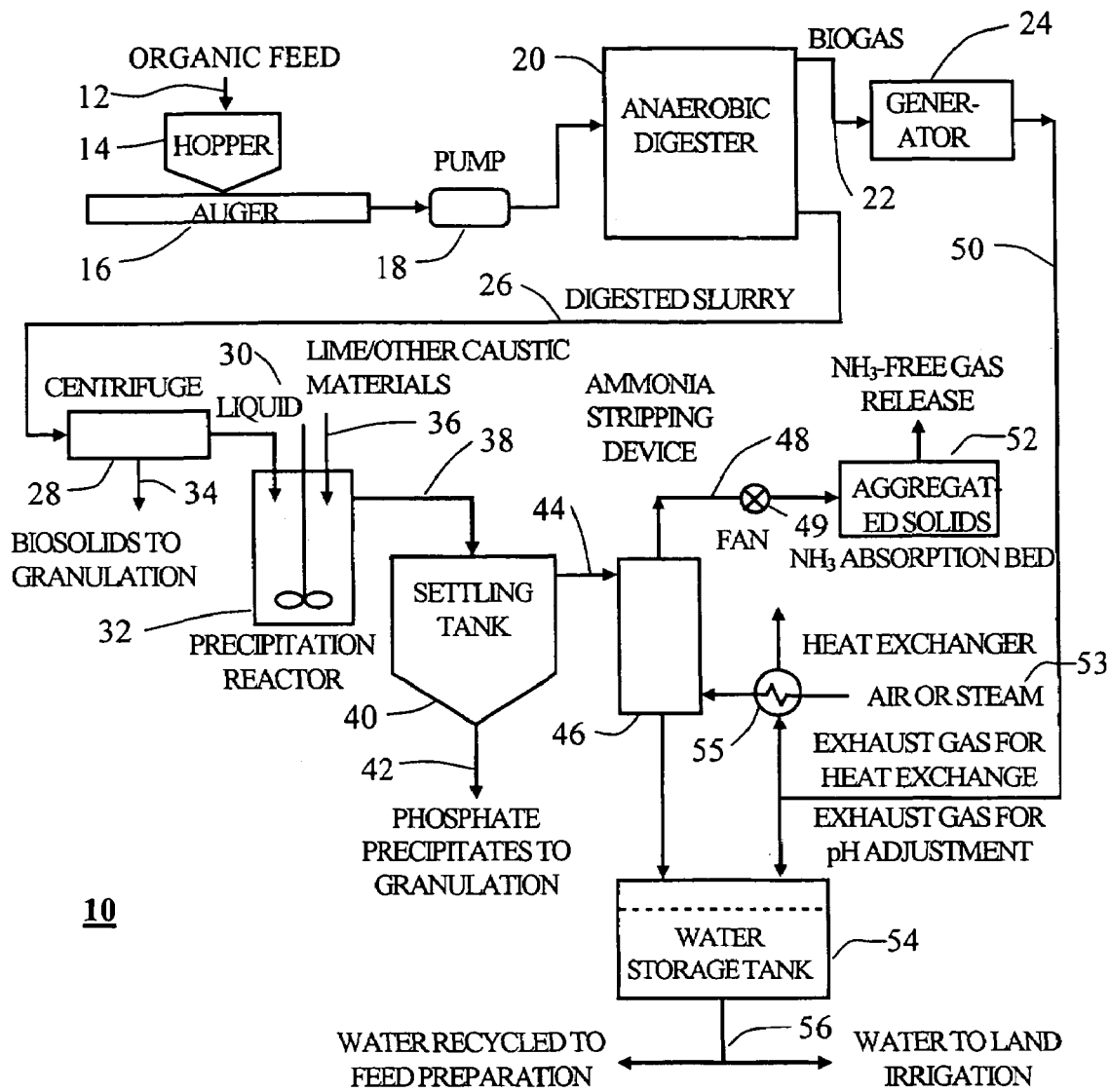
FIG. 1 is a block diagram of a process for removal and recovery of nutrients from digested manure or other organic wastes in accordance with the teachings of the present invention.

The preferred process for removal and recovery of nutrients from digested manure or other organic wastes, referred to generally by reference character 10, will now be described with reference to FIGS. 1 and 2.

Referring to FIG. 1, the process for removal and recovery of nutrients (N, P) and recycling water from digested manure or other organic wastes 10 is shown. It integrates lime precipitation, ammonia stripping, bio-absorption using aggregated solids and pH adjustment using exhaust gas from a co-generation system. Organic feed 12 is fed into a hopper 14 which is connected to an auger 16. A pump 18 such as a progressive cavity pump moves feed 12 to an anaerobic digester 20. From the anaerobic digester 20, biogas 22 is fed to a generator 24, such as a co-generation system, while the digested slurry 26 is fed into a centrifuge 28. The centrifuged digested liquid 30 after solid/liquid separation goes into a precipitation reactor 32 with additives 36 such as lime combined with wood ash or some other low-cost material instead of wood ash. The mixture 38 is moved to a settling tank 40, where generated calcium phosphate solids 42 are separated from liquid 44. The settled solids 42 have higher nutrient value. Then, liquid 44 goes through a stripping device 46 to strip out the excess ammonia 48. The stripping device can be a stripping tower or other stripping unit. If air is used as the stripping medium 53, it can be directly or indirectly heated up by high temperature exhaust 50 gas from the co-generator 24 through heat exchanger 55. In the case of direct heating, exhaust gas 50 will be part of the stripping gas 53 after mixing with the incoming air. This stripping process allows the removal of high $NH_4$ content, up to 3000 ppm from digested slurry 26. This continuous process allows the removal of both N and P from the digested slurry 26. After stripping device 46, the pH of the liquid stream is reduced to around 7 in water storage tank 54 with exhaust gas 50 containing $CO_2$ from the co-generation system 24. This injection of exhaust gas 50 will increase temperature of the liquid 56, now treated water, which can be recycled back to the hopper 14 to prepare feed 12. Water 56 may also be used in irrigation. The ammonia-enriched gas 48 will be pumped by fan 49 into a column 52 filled with aggregated-centrifuged solid. Nitrogen will be recovered through absorption process. The resultant solids contain higher nitrogen content.

Figure 2:
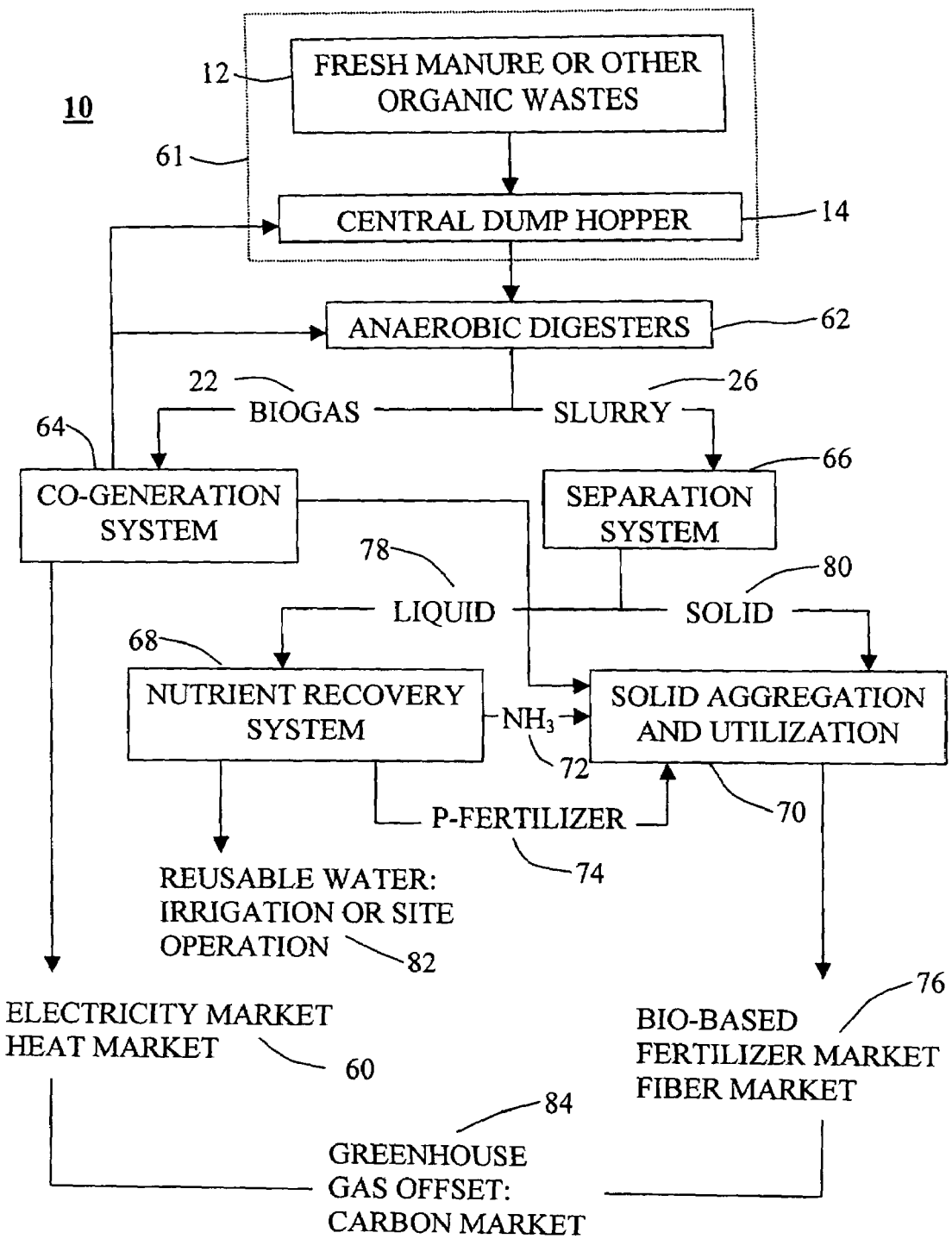
FIG. 2 is a flow diagram of a process for removal and recovery of nutrients from digested manure or other organic wastes in accordance with the teachings of the present invention.

Referring now to FIG. 2, this nutrient recovery and water recycle system can be combined into an integrated comprehensive manure utilization system(IMUS), which consists of seven major components: manure (organic materials)handling 61, biogas production 62, biogas utilization 64, liquid/solid separation 66, nutrient recovery system 68, bio-based fertilizer production 70 and an integrating system 10. Fresh manure or organic materials 61 enters dump hopper 14. The dump hopper 14 is equipped to adjust temperature and solid/liquid ratio of manure to a predetermined level. Biogas production is achieved through anaerobic digestion in anaerobic digesters 20. The temperature in the anaerobic digesters is maintained at 55 to 60° C., which is to create an optimal growth temperature for a consortium of thermophilic bacteria. This condition will shorten the hydraulic retention time in digester 20, destroy over 99% of pathogens present in raw manure and maximize biogas production. Biogas 22 utilization includes a co-generation unit 64, which is connected to the electrical grid 60, and a heat exchanger system, which allows delivery of waste heat produced by the co-generation unit to digesters 20, hopper 14 and fertilizer production system 70. After the anaerobic digestion that produces biogas 22, the remaining material is transferred to a centrifuge system 66 with the addition of polymers for liquid 78 and solid 80 separation. Liquid 78 is then treated in the nutrient recovery system 68 through physical and chemical processes to recover nitrogen 72 and phosphate 74 and produce reusable water 82. Solids 80 are processed through aggregation process combined with a nutrient enrichment process, if required, to produce solid bio-based fertilizer 76 with balanced nutrients. Bio-based fertilizer 76 will be produced in different forms and moisture contents depending on the end uses and transportation requirements. The rate of nutrient release from the bio-based fertilizers is controlled by the aggregate size and density. The last component is to integrate all these processes and optimize each component and make anaerobic digestion, nutrient recovery and water recycling from manure or other organic wastes an economically viable operation. This integrated process will mitigate greenhouse gas emissions 84 and reduce other negative environmental impacts associated with manure and organic waste management.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent to one skilled in the art that modifications may be made to the illustrated embodiment without departing from the spirit and scope of the invention as hereinafter defined in the Claims.

The embodiments of the invention in which an exclusive property or privilege is claimed are defined as follows:

1. A process for removal and recovery of nutrients from digested manure or other organic wastes, comprising the steps of:

(a) separating waste from an anaerobic digester into digested liquids, digested solids and biogas;

(b) precipitating solids from the digested liquids;

(c) stripping ammonia from the digested liquids;

(d) injecting a stream of carbon dioxide into the digested liquids to reduce the pH;

(e) recycling the digested liquids back to the anaerobic digester for use in diluting in coming solid wastes; and (f) passing the ammonia stripped from the digested liquid through the digested solids and precipitated solids to recover nitrogen through absorption with the resultant solids being usable as a biofertilizer with a high nitrogen content.

2. The process as defined in claim 1 further comprising the step of operating a co-generation system which is fuelled by the captured biogas to produce a flue gas comprising carbon dioxide, which flue gas is the source of carbon dioxide in step (d).

3. The process of claim 1 wherein the flue gas is used to directly or indirectly heat the digested liquid when ammonia stripping in step (c).

4. The process of claim 3 wherein the flue gas is mixed with air and used to air strip ammonia from the digested liquids.

5. The process of claim 3 wherein the flue gas is used in a heat exchanger to heat the digested liquids in the ammonia stripping step.

* * * * *